United States Patent [19]

Legan et al.

[11] 4,330,152
[45] May 18, 1982

[54] SUPPORT AND RESTRAINT APRON

[76] Inventors: Sandra K. Legan, 335 Bard St., Fillmore, Calif. 93015; Delores M. Diehl, 500 W. Santa Maria, Santa Paula, Calif. 93060

[21] Appl. No.: 174,742

[22] Filed: Aug. 4, 1980

[51] Int. Cl.³ .......................................... A47C 31/00
[52] U.S. Cl. ...................................... 297/465; 297/484
[58] Field of Search ................ 297/465, 484; 128/134, 128/133

[56] References Cited

U.S. PATENT DOCUMENTS

| | | | |
|---|---|---|---|
| 2,252,357 | 8/1941 | Shaw | 128/134 |
| 2,851,033 | 9/1958 | Posey | 128/134 |
| 2,853,068 | 9/1958 | Povel | 128/134 |
| 3,125,373 | 3/1964 | Boatman | 297/465 |
| 3,191,599 | 6/1965 | Kendall | 297/484 X |
| 3,265,065 | 8/1966 | Jillson | 128/134 |
| 3,276,431 | 10/1966 | Murcott | 128/134 |
| 3,276,432 | 10/1966 | Murcott | 128/134 X |
| 3,565,483 | 2/1971 | Posey | 297/484 |
| 4,050,737 | 9/1977 | Jordan | 297/465 |

Primary Examiner—James T. McCall
Attorney, Agent, or Firm—Jack C. Munro

[57] ABSTRACT

An apron for supporting and restraining an elderly or injured person in a sitting position within a chair. The apron includes a main body section from which extends two free-ended straps and two looped straps. The body section is to be placed adjacent the chest area of the user and the free-ended straps are to be located in a crossed relationship across the back of the chair. Each free-ended strap is to then extend through a looped strap with the free ends of the free-ended straps being secured together. One of the free-ended straps includes a quick release means which can be quickly disengaged for quick removal of the person within the chair.

6 Claims, 4 Drawing Figures

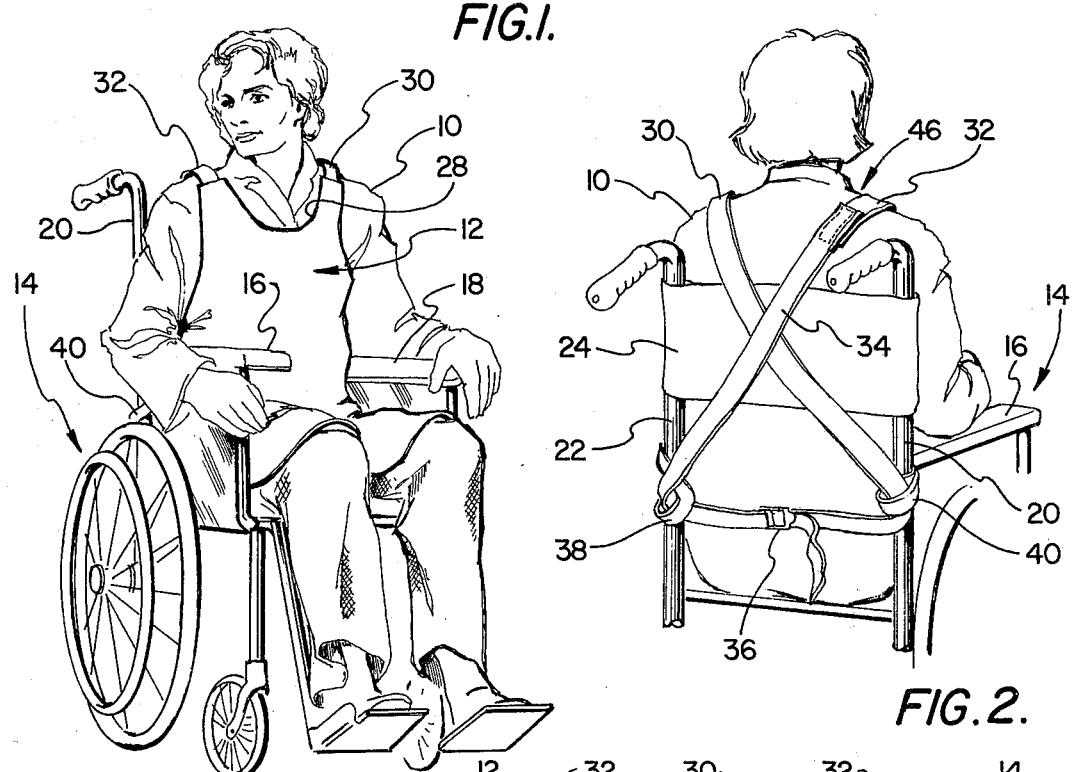
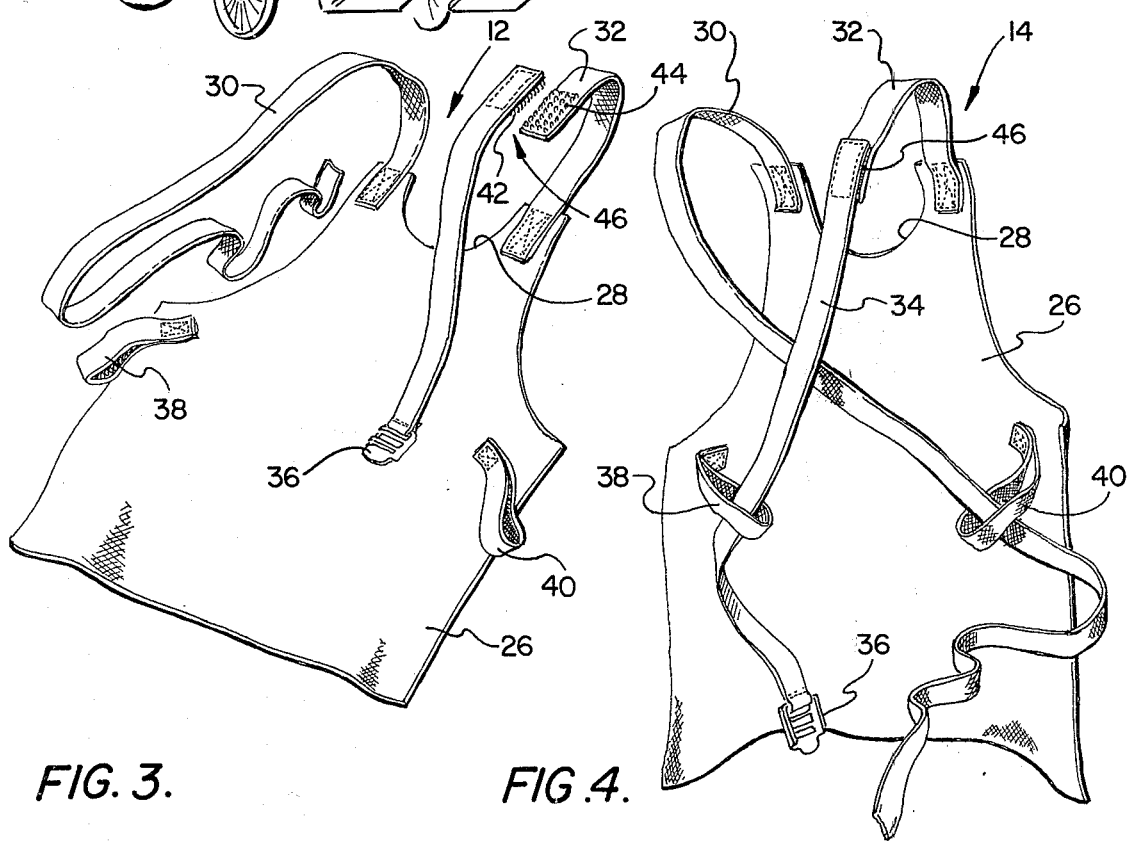

SUPPORT AND RESTRAINT APRON

BACKGROUND OF THE INVENTION

Elderly, injured or sick people may find it difficult to sit in a chair. Such an individual may not be able to hold his upper torso in the upright position. As a result, the upper torso can move laterally or forward with respect to the chair causing the individual to actually fall from the chair. There have been cases where people have become very seriously injured in such a situation.

In the past, in order to overcome this problem, it has been common to strap the patient to the chair. This usually takes the form of two separate straps, one located about the chest area to secure the patient to the chair. Also, arm straps may be employed.

The use of such prior art strapping arrangements have many disadvantages, not the least of which is the undesirable psychological affect on the patient of being strapped to a chair. Another disadvantage arises if there is ever a need to quickly remove the patient from the chair; such is difficult to do because of the requirement to disengage so many different straps. Also, another disadvantage is that the straps totally immobilize the patient. Such total immobility is not required and if a very small amount of mobility could be given to the patient, such would be desirable.

There is a need for a support and a restraint device to be used in conjunction with a chair, such as a wheelchair, which would securely restrain the patient in an upright position but yet provide a limited amount of movement of the patient and would also not make the patient feel totally confined.

SUMMARY OF THE INVENTION

The support and restraint apron of the present invention takes the form of a sheet material body section which has an exterior surface, an interior surface, an upper edge and side edges. The interior surface of the main body section is to be positioned against the chest area of the patient. A pair of free-ended straps are attached to the upper edge. Attached to the interior surface adjacent each lateral side is a looped strap. The pair of free-ended straps are to be located in a crossed relationship about the back of the chair with each free-ended strap to pass through a looped strap. The then attached free ends of the free-ended straps are then secured together by means of a buckle fastening assembly. One of the free-ended straps also includes a quick release means which when activated permits quick removal of the patient from the chair.

The primary objective of this invention is to construct an apron which securely restrains an individual in an upright position in a chair and will prevent the individual from falling from the chair.

Another objective of this invention is to construct an apron which does securely restrain an individual in the chair while permitting the individual a limited amount of movement.

Another objective of this invention is to construct an apron which can be quickly and easily disengaged from the chair.

BRIEF DESCRIPTION OF THE DRAWING

FIG. 1 is a front perspective view of an individual supported and restrained within a wheelchair by the apron of the present invention;

FIG. 2 is a rear perspective view of the individual shown within FIG. 1;

FIG. 3 is a rear perspective view of the apron of this invention showing the straps in the disconnected state; and FIG. 4 is a rear perspective view of the apron of this invention showing the straps in their approximate position during use.

DETAILED DESCRIPTION OF THE SHOWN EMBODIMENT

Referring particularly to the drawing, there is shown a patient 10 which is supported in a conventional wheelchair 14. The wheelchair 14 has arms 16 and 18 which are respectively attached to a back rods 20 and 22. The pair of back rods 20 and 22 are connected together through a back support plate 24. The arms of the patient 10 are to be capable of being supported on the wheelchair arms 16 and 18.

The individual 10 is to be supported within the chair 14 by the apron 12. The apron 12 includes a main body section 26 which is constructed of a sheet material, such as a fabric. The main body section 26 has an upper edge which includes a recess 28. The recess 28 is to be located adjacent the neck area of the patient 10. The body section 26 also includes lateral edges and a bottom edge.

A first free-ended strap 30 is fixedly secured adjacent the upper edge of the main body section 26 on one side of the recess 28. A second free-ended strap being formed of an upper strap 32 and a lower strap 34 is fixedly secured also adjacent the upper edge of the main body section 26 on the opposite side of the recess 28. The physical length of the free-ended strap 30 is greater than the combined physical length of the straps 32 and 34. The free-end of the strap 34 has a buckle 36 attached thereto. The buckle is deemed to be conventional and forms no specific novelty in respect to this invention.

Attached to the interior surface of the main body section 26 are a first looped strap 38 and a second looped strap 40. The looped strap 38 is located adjacent one lateral edge of the main body section 26 with the second looped strap being located adjacent the opposite lateral edge of the main body section 26.

The first free-ended strap 30 is to extend over the left shoulder of the patient and extend through the loop 40 as shown in FIG. 2. The second strap in the form of the straps 32 and 34 is to extend over the right shoulder and pass through the loop 38. The free end of the strap 34 is then connected with the buckle 36 and pulled tight. It is to be noted that the loop 40 extends around the post 20 just under arm 16. Similarly, the loop 38 extends under arm 18 around the post 22. When the strap 34 and the strap 30 are pulled tight in relation to the buckle 36, the individual 10 is supported and restrained and is secured to the wheelchair 14. It is to be noted that the frontal appearance of the main body section 26 of the apron is such that there are no visable tie-down straps which psychologically gives the individual the feeling of not being totally restrained.

Secured to the free end of the strap 32 is a strip 42 and a second strip 44 is attached to the strap 34. The strips 42 and 44 form a fastening means 46. The strip 42 may take the form of a mass of tiny eyelets with the strip 44 taking the form of a mass of tiny hooks. The hooks and eyelets when pressed together tightly secure the strap 32 to the strap 34. This type of a connection is frequently sold under the trade name of "VELCRO".

The purpose of the connection 46 is that, if for some reason (such as a medical emergency), it is important to remove the patient as quickly as possible from the wheelchair 14, that another individual only needs to grasp the strap 34 adjacent the connection 46 and quickly jerk such in an outward manner. This results in strap 34 disengaging from the strap 32 which will then free the entire apron permitting the individual 10 to be removed from the wheelchair.

It is to be understood that the length of the strap 30 will be sufficient so as to accommodate even the most obese individual. The actual material of construction of the entire apron 12 will be fabric. But, the material of construction is deemed to be a matter of choice.

What is claimed is:

1. In combination with a chair, a person to occupy the chair, said chair having a pair of spaced-apart arms, each said arm having an upper surface and a lower surface, said arms are positioned so the person's elbows are capable of resting on said upper surfaces, a support and restraint apron for the person comprising:

a sheet material body section to be positioned against the chest area of the person, said sheet material body section having an exterior surface and an interior surface, said interior surface to be located directly against the person, said body section having an upper edge and right edge and a left edge;

a first strap attached to said upper edge directly adjacent said left edge and adapted to be located directly adjacent the left side of the neck of the person, a second strap attached to said upper edge directly adjacent said right edge and adapted to be located directly adjacent the right side of the neck of the person, said first and second straps to be located in a crossed relationship exteriorly of the back of said chair;

a first loop attached to said interior surface adjacent said left edge, a second loop attached to said interior surface adjacent said right edge, both said first and second loops being located in the waist area of the person, said first loop to be conducted beneath a said arm to be located directly adjacent its said lower surface, said second loop to be conducted beneath the other said arm to be located directly adjacent its said lower surface, said first strap to pass through said second loop and said second strap to pass through said first loop; and attaching means securing together the free ends of said first and second straps.

2. In combination with a chair, a person to occupy the chair, a support and restraint apron for the person comprising:

a sheet material body section to be positioned against the chest area of the person, said sheet material body section having an exterior surface and an interior surface, said interior surface to be located directly against the person, said body section having an upper edge, and a right edge and a left edge;

a first strap attached to said upper edge and adapted to be located directly adjacent one side of the neck of the person, a second strap attached to said upper edge and adapted to be located directly adjacent the other side of the neck of the person, said first and second straps to be located in a crossed relationship about the back of said chair;

a first loop attached to said interior surface adjacent said right edge, a second loop attached to said interior surface adjacent said left edge, both said first and second loops being located in the waist area of the person, said first strap to pass through said second loop and said second strap to pass through said first loop;

attaching means securing together the free ends of said first and second straps; and quick release means connected to said first strap and separate from said attaching means, whereby operation of said quick release means disengages said apron from said chair permitting said person to be then removed from said chair.

3. The combination as defined in claim 2 wherein said quick release means comprises:

said first strap being divided into an upper strap and a lower strap, said upper strap being normally secured to said lower strap by securing means, said securing means being quickly and manually operable to effect disengagement of said upper strap from said lower strap.

4. The combination as defined in claim 3 wherein:

said securing means comprising interengaging strips of hooks and eyelets.

5. The combination as defined in claim 1 wherein:

said upper edge including a neck locating recess, said first strap being located on one side of said recess, said first strap being located on one side of said recess with said second strap being located on the other side of said recess.

6. The combination as defined in claim 4 wherein:

said upper edge including a neck locating recess, said first strap being located on one side of said recess with said second strap being located on the other side of said recess.

* * * * *